(12) United States Patent
Ellwood et al.

(10) Patent No.: US 10,227,280 B1
(45) Date of Patent: Mar. 12, 2019

(54) PROCESS FOR PREPARING SPIROGALBANONE

(71) Applicant: Givaudan, S.A., Vernier (CH)

(72) Inventors: Simon Ellwood, Kilchberg (CH); William Alexander Thiam, Vernier (CH)

(73) Assignee: Givaudan, S.A., Vernier (CH)

( * ) Notice: Subject to any disclaimer, the term of this patent is extended or adjusted under 35 U.S.C. 154(b) by 0 days.

(21) Appl. No.: 16/070,687

(22) PCT Filed: Feb. 13, 2017

(86) PCT No.: PCT/EP2017/053112
§ 371 (c)(1),
(2) Date: Jul. 17, 2018

(87) PCT Pub. No.: WO2017/140607
PCT Pub. Date: Aug. 24, 2017

(30) Foreign Application Priority Data

Feb. 15, 2016 (GB) .................... 1602644.5

(51) Int. Cl.
| C07C 45/00 | (2006.01) |
| C07C 41/30 | (2006.01) |
| C07C 45/51 | (2006.01) |
| C07C 41/01 | (2006.01) |
| C07C 41/18 | (2006.01) |
| C07C 49/557 | (2006.01) |

(52) U.S. Cl.
CPC ............ *C07C 45/513* (2013.01); *C07C 41/01* (2013.01); *C07C 41/18* (2013.01); *C07C 41/30* (2013.01); *C07C 49/557* (2013.01); *C07C 2602/50* (2017.05)

(58) Field of Classification Search
CPC .... C07C 45/513; C07C 41/30; C07C 2602/50
See application file for complete search history.

(56) References Cited

U.S. PATENT DOCUMENTS

| 4,147,672 A | 4/1979 | Schulte-Elte et al. |
| 4,264,467 A | 4/1981 | Schulte-Elte et al. |
| 4,289,659 A | 9/1981 | Schulte-Elte et al. |
| 2013/0310293 A1 | 11/2013 | Birkbeck |

FOREIGN PATENT DOCUMENTS

| EP | 0913383 A1 | 5/1999 |
| WO | WO/2012110281 A1 | 8/2012 |

OTHER PUBLICATIONS

PCT/EP2017/053112—International Search Report, dated Apr. 11, 2017.
PCT/EP2017/053112—International Written Opinion, dated Apr. 11, 2017.
GB1602644.5—Great Britain Search Report, dated Dec. 5, 2016.

*Primary Examiner* — Sikarl A Witherspoon
(74) *Attorney, Agent, or Firm* — Curatolo Sidoti Co., L.P.A.; Joseph G. Curatolo; Salvatore A. Sidoti

(57) ABSTRACT

A method of making spirogalbanone includes the steps of:
(a) subjecting ethynylspirodecanol to a Rupe rearrangement to give a compound of the formula I

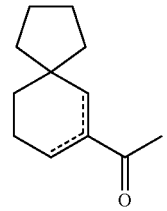

I (b) converting the compound of (a) to a C1-C4 alkyl acetal;
(c) subjecting the acetal to a trans-acetalization reaction with allyl alcohol in the presence of a mild acid catalyst;
(d) heating the product of (c) in the presence of an acid catalyst to give an allylenolether; and
(e) subjecting the product of (d) to a Claisen rearrangement to give spirogalbanone.

The method affords an easier and more efficient method of preparation.

8 Claims, No Drawings

PROCESS FOR PREPARING SPIROGALBANONE

CROSS REFERENCE TO RELATED APPLICATIONS

This application is a national stage application of International Application No. PCT/EP2017/053115, filed 13 Feb. 2017, which claims priority from Great Britain Patent Application No. GB 1602644.5, filed 15 Feb. 2016, which applications are incorporated herein by reference.

This disclosure relates to a process of preparing spirogalbanone.

Spirogalbanone:

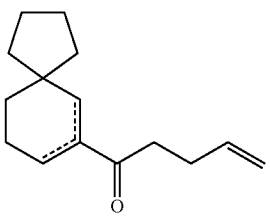

is a fragrance ingredient with a potent galbanone note that is much valued in perfumery. It exists in two isomers, (1-(spiro[4,5]dec-6-en-7-yl)-4-penten-1-one and 1-(spiro[4,5]dec-7-en-7-yl)-4-penten-1-one). The latter is the more powerful, and the two typically occur in commercial formulations in the weight ratio of 40:60. Complete separation is possible, but rarely worthwhile.

One typical method currently in use for the manufacture of spirogalbanone may be summarized as follows:

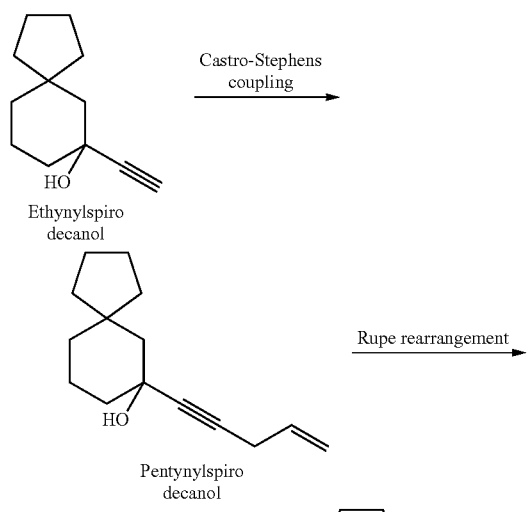

It has now been found that spirogalbanone may be made by a new and more efficient method. There is therefore provided a method of making spirogalbanone comprising the steps of:

(a) subjecting ethynylspirodecanol to a Rupe rearrangement to give a compound of the formula I

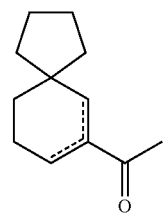

(b) converting the compound of (a) to a C1-C4 alkyl acetal;
(c) subjecting the acetal to a trans-acetalisation reaction with allyl alcohol in the presence of a mild acid catalyst;
(d) heating the product of (c) in the presence of an acid catalyst to give an allylenolether; and
(e) subjecting the product of (d) to a Claisen rearrangement to give spirogalbanone.

The Rupe rearrangement is the acid-catalysed rearrangement of tertiary α-acetylenic alcohols to give α,β-unsaturated ketones (see, for example, H. Rupe and K. Glenz, *Justus Liebigs Ann. Chem.*, 436, 195 (1924)).

The Claisen rearrangement is a [3,3]-sigmatropic rearrangement in which an allyl vinyl ether is converted thermally to an unsaturated carbonyl compound. It was originally reported by L. Claisen in the *Berichte der deutschen chemischen Gesellschaft*, 45, 3, pp. 3157-3166 (October-December 1912), and has since been the subject of much work and numerous variations. In the present disclosure, it comprises the final stage, as will be further described hereinunder.

Ethynylspirodecanol (9-ethynylspiro[4.5]decan-9-ol) may be prepared according to the method described in EP 0 913 383.

In the Rupe rearrangement, the ethynylspirodecanol is heated under aqueous acidic conditions. Acids used are typically organic acids, such as formic and acetic acids, followed by heating and extracting with alkane.

The product of stage (a), the compound of formula I, is a mixture of the compound of Formula I (comprising about 75% by weight of the product) and other side-products, most of this remainder being a tarry residue. The compounds of Formula I, which comprise from 70-75% by weight of the final product, may be isolated by means of flash distillation. The mixture comprises about 60-65% of the compound of Formula Ib and the remainder formula Ia:

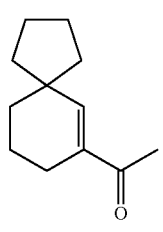

1-(spiro[4.5]dec-6-en-7-yl)ethanone

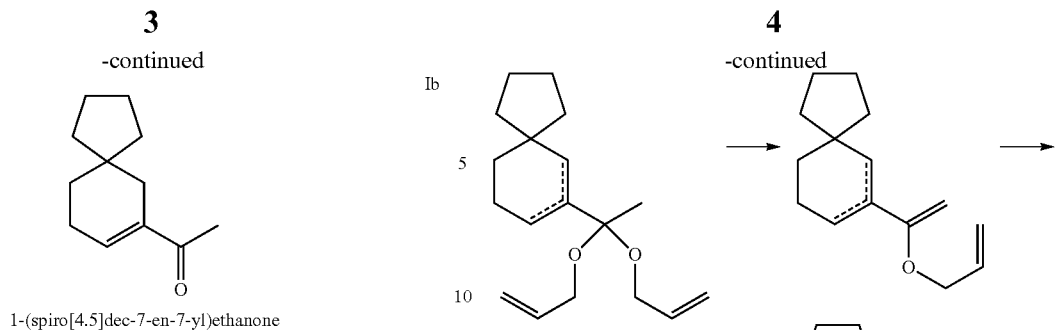

1-(spiro[4.5]dec-7-en-7-yl)ethanone

The use of the expression "compound of Formula I" is hereinafter used in the sense of encompassing both compounds Ia and Ib.

It is possible to isolate the compound of Formula I by distillation before proceeding with the preparation of spirogalbanone, and this will result in a slightly better yield of spirogalbanone, but the preparation may proceed with the crude product.

The compound of Formula I is a novel compound, which itself has interesting odour properties, described as fruity, camomile, agrestic, leathery, fatty. There is therefore also provided a compound of the formula I, as hereinabove defined.

The compound of Formula I is then subjected to the following series of reactions:

They are converted to C1-C4 alkyl acetal;

This acetal is trans-acetalised with allyl alcohol in the presence of a mild acid catalyst;

The resulting product is heated in the presence of an acid catalyst to give an allylenolether; and The resulting product is subjected to a Claisen rearrangement to give spirogalbanone.

It should be noted that by "C1-C4 alkyl acetal" is meant a compound of the formula III

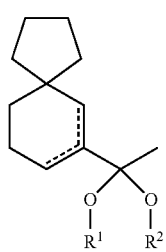

in which $R^1$, $R^2$ may be the same or different C1-C4 alkyl.

A typical reaction sequence is shown in the following scheme:

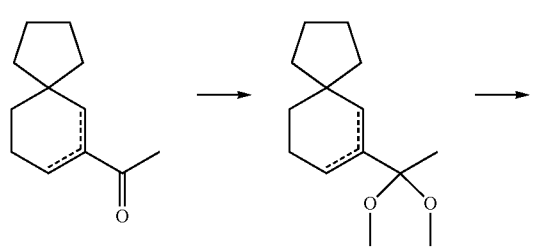

In this illustration, the C1-C4 alkyl comprises two methyl groups and both methyl groups are replaced by allyl groups. In some cases, only one alkyl group is replaced, but this has no effect on the final result, which is still spirogalbanone.

The various steps in the sequence are well known to the art and can be carried out according to the normal practices of the art. They may be performed sequentially in a single reaction vessel, without the need for any purification or isolation of intermediates. The method hereinunder described is one of a number of possible routes to achieving the desired end result, all of which are encompassed herein.

The acetal formation may be achieved by any convenient method, a particular method being the reaction of the parent ketone with an alcohol and the corresponding trialkylorthoformate in the presence of a strong acid catalyst. Any such strong acid catalyst may be used, particular examples being liquid catalysts, such as sulphuric acid and methanesulphonic acid. This reaction is typically carried out at low temperatures, particularly under 0° C., more particularly between −10° C. and −5° C.

When reaction is complete (typically of the order of 6 hours), the catalyst is neutralized by addition of a base, such as sodium acetate.

The transacetalisation and elimination steps may be performed together. This is typically achieved by adding to the mixture a mild acid catalyst and allyl alcohol. The temperature is raised to 20-25° C. prior to the allyl alcohol addition, gradually raising the temperature to about 130-150° C. after the addition and maintaining it there, while distilling off alcoholic by-products. Typical suitable catalysts for this stage include citric and propionic acids.

Time for this step varies, 6-12 hours being typical, but more than 12 hours is possible.

Heating is continued, and the Claisen rearrangement then takes place spontaneously.

The final result is spirogalbanone at a chemical (molar) yield of greater than 95%.

As mentioned hereinabove, the method allows the preparation of spirogalbanone in a more efficient and less expensive method.

The disclosure is further described with reference to the following non-limiting examples in which all parts are by weight.

(a) Preparation of Compound of Formula I:

A reactor was charged with 714 parts formic acid and 161 parts water. The temperature was raised to 95-100° C. and 500 parts ethynylspirodecanol (86.6% by weight) were added over a period of 30 minutes. The temperature was maintained until reaction was complete (about 9 hours).

The reaction mixture was then cooled to 30-40° C. and 250 parts each of 10% brine and heptane were added. The mixture was stirred for 15 minutes and allowed to settle for 15 minutes, at which point the lower (aqueous) layer was run off. To this aqueous layer, a further 300 parts of heptane was then added, and the 15 minutes stirring/15 minutes settle/aqueous layer drain repeated. The resulting two organic fractions were combined and washed three times each with 250 parts 10% brine. The solvent was removed in a rotary evaporator to give 481 parts of crude material (65-70% pure). The crude material was flash distilled to give 322 parts of the compound of Formula I (70% yield at 90% purity)

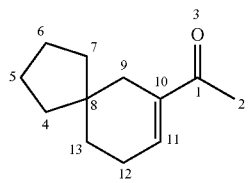

$^1$H NMR (400 MHz, CDCl$_3$) (major isomer): δ 6.91 (tt, J=3.9, 1.7 Hz, 1H, 11-CH=), 2.34-2.28 (m, 2H, 12-CH$_2$—), 2.29 (s, 3H, 2-CH$_3$), 2.12-2.10 (m, 2H, 9-CH$_2$—), 1.67-1.58 (m, 4H, 5-CH$_2$—, 6-CH$_2$—), 1.49-1.45 (m, 2H, 13-CH$_2$—), 1.39-1.34 (m, 4H, 4-CH$_2$—, 7-CH$_2$—) ppm.

$^{13}$C NMR (100 MHz, CDCl$_3$) (major isomer): δ 199.1 (s, 1-C=O), 140.3 (d, 11-CH=), 139.0 (s, 10-C=), 40.3 (s, 8-C—), 37.9 (2t, 4-CH$_2$, 7-CH$_2$), 35.0 (t, 9-CH$_2$), 32.6 (t, 13-CH$_2$), 25.0 (q, 2-CH$_3$), 24.6 (t, 12-CH$_2$), 24.1 (2t, 5-CH$_2$, 6-CH$_2$) ppm.

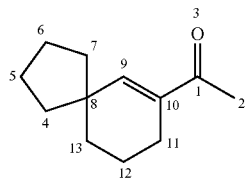

$^1$H NMR (400 MHz, CDCl$_3$) (minor isomer): δ 6.62 (t, 1H, J=1.5 Hz, 9-CH=), 2.28 (s, 3H, 2-CH$_3$), 2.18 (td, J=6.2, 1.7 Hz, 2H, 11-CH$_2$—), 1.75-1.70 (m, 4H, 5-CH$_2$—, 6-CH$_2$—), 1.67-1.52 (m, 6H, 4-CH$_2$—, 7-CH$_2$—, 12-CH$_2$—), 1.48-1.45 (m, 2H, 13-CH$_2$—) ppm.

$^{13}$C NMR (100 MHz, CDCl$_3$) (minor isomer): δ 199.3 (s, 1-C=O), 149.4 (d, 9-CH=), 137.0 (s, 10-C=), 44.1 (s, 8-C—), 39.8 (2t, 4-CH$_2$—, 7-CH$_2$—), 34.0 (t, 13-CH$_2$—), 24.9 (q, 2-CH$_3$), 24.4 (2t, 5-CH$_2$—, 6-CH$_2$—), 23.0 (t, 11-CH$_2$—), 20.0 (t, 12-CH$_2$—) ppm.

(b) Preparation of Spirogalbanone 362.1 parts of the compound of Formula I prepared as previously described was added to a reactor with 94.6 parts methanol, and the mixture cooled to −8° C. under nitrogen. 2.8 parts 98% sulphuric acid was then added and the temperature maintained within the range −5 to −10° C. To this mixture 252.8 parts of trimethyl orthoformate was added over a period of 2 hours, and the mixture stirred at this temperature for 3.5 hours.

The temperature was then raised to 0° C. over a period of 20 minutes and 8.4 parts sodium acetate added. Stirring at 0° C. was continued for 30 minutes, during which time the colour of the reaction mixture changed from black-grey to clear orange. The pH was checked to ensure that it is 3 minimum, with more sodium acetate being added to maintain this pH, if necessary The temperature of the reaction mixture was raised to 20-25° C. and 249.7 parts allyl alcohol and 2.9 parts citric acid added. The temperature was then slowly raised to 150° C. over a period of 7 hours with distillation. The mixture was sampled regularly and checked by GC analysis. When the amount of product remained the same (within 1% difference), the reaction was stopped by cooling to 40° C. and adding 200 parts heptane and 340 parts water. The mixture was stirred for 15 minutes, allowed to settle for a further 15 minutes and the lower (aqueous) layer drained. This process was repeated with the aqueous layer with 100 parts heptane. The two heptane layers were then combined and washed with 340 parts of 10% brine, followed by 300 parts 10% sodium carbonate solution.

Solvent was distilled off in a rotary evaporator, to give 484.3 parts oil.

50 parts of paraffin oil was added to the oil and the mixture subjected to flash distillation by means of a 3 cm Vigreux column at 1 mbar pressure to give 351.8 parts spirogalbanone in the fractions. Yield was 90.4%

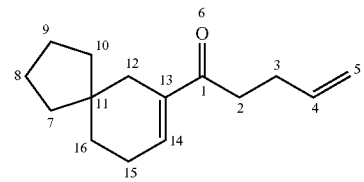

$^1$H NMR (400 MHz, CDCl$_3$) (major isomer): δ 6.90 (tt, J=3.9, 1.7 Hz, 1H, 14-CH=), 5.89-5.78 (m, 1H, 4-CH=), 5.07-5.00 (m, 1H, 5=CH$_a$), 4.98-4.94 (m, 1H, 5=CH$_b$), 2.74 (t, J=7.8 Hz, 2H, 2-CH$_2$), 2.38-2.28 (m, 4H, 3-CH$_2$, 15-CH$_2$), 2.12-2.11 (m, 2H, 12-CH$_2$), 1.68-1.53 (m, 4H, 8-CH$_2$—, 9-CH$_2$—), 1.49-1.45 (m, 2H, 16-CH$_2$—), 1.39-1.34 (m, 4H, 7-CH$_2$—, 10-CH$_2$—) ppm.

$^{13}$C NMR (100 MHz, CDCl$_3$) (major isomer): δ 200.4 (s, 1-C=O), 139.2 (d, 14-CH=), 138.6 (s, 13-C=), 137.5 (d, 4-CH=), 114.7 (t, 5=CH$_2$), 40.4 (s, 11-C—), 38.0 (2t, 7-CH$_2$, 10-CH$_2$), 36.2 (t, 2-CH$_2$), 35.2 (t, 12-CH$_2$), 32.7 (t, 16-CH$_2$), 28.6 (t, 3-CH$_2$), 24.6 (t, 15-CH$_2$), 24.2 (2t, 8-CH$_2$, 9-CH$_2$) ppm.

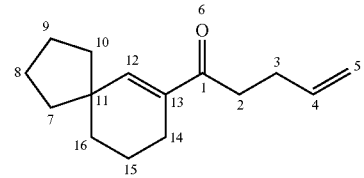

$^1$H NMR (400 MHz, CDCl$_3$) (minor isomer): δ 6.62 (t, 1H, J=1.5 Hz, 12-CH=), 5.89-5.78 (m, 1H, 4-CH=), 5.07-5.00 (m, 1H, 5=CH$_a$), 4.98-4.94 (m, 1H, 5=CH$_b$), 2.74 (t, J=7.8 Hz, 2H, 2-CH$_2$), 2.38-2.32 (m, 2H, 3-CH$_2$—), 2.19 (td, J=6.4, 1.7 Hz, 2H, 14-CH$_2$—), 1.74-1.71 (m, 4H, 8-CH$_2$—, 9-CH$_2$—), 1.67-1.51 (m, 6H, 7-CH$_2$—, 10-CH$_2$—, 15-CH$_2$—), 1.49-1.45 (m, 2H, 16-CH$_2$—) ppm.

$^{13}$C NMR (100 MHz, CDCl$_3$) (minor isomer): δ 200.6 (s, 1-C=O), 148.3 (d, 12-CH=), 137.6 (d, 4-CH=), 136.6 (s, 13-C=), 114.7 (t, 5-CH$_2$=), 44.1 (s, 11-C—), 39.9 (2t, 7-CH$_2$, 10-CH$_2$), 36.1 (t, 2-CH$_2$), 34.2 (t, 16-CH$_2$), 28.5 (t, 3-CH$_2$), 24.5 (2t, 8-CH$_2$, 9-CH$_2$), 23.3 (t, 14-CH$_2$), 20.0 (t, 15-CH$_2$) ppm.

The invention claimed is:

1. A method of making spirogalbanone comprising the steps of:
   (a) subjecting ethynylspirodecanol to a Rupe rearrangement to give a compound of the formula I

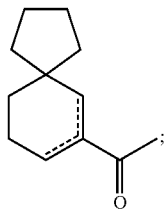

(b) converting the compound of (a) to a C1-C4 alkyl acetal;
   (c) subjecting the acetal to a trans-acetalisation reaction with allyl alcohol in the presence of a mild acid catalyst;
   (d) heating the product of (c) in the presence of an acid catalyst to give an allylenolether; and
   (e) subjecting the product of (d) to a Claisen rearrangement to give spirogalbanone.

2. The method according to claim 1, in which the acetal formation of step (b) is caused by the reaction of the compound of Formula I with an alcohol and a corresponding trialkylorthoformate in the presence of a strong acid catalyst.

3. The method according to claim 1, in which step (b) is carried out at a temperature below 0° C.

4. The method according to claim 1, in which steps (c) and (d) are performed together.

5. A compound of the formula I

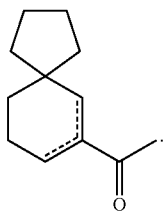

6. The compound according to claim 5 selected from the compounds of Formulae Ia and Ib:

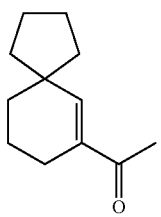

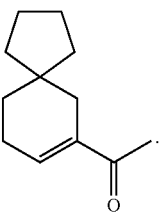

7. The method according to claim 1, in which step (b) is carried out at a temperature between −10° and −5° C.

8. The method according to claim 2, wherein the strong acid catalyst is selected from at least one of sulphuric acid and methanesulphonic acid.

* * * * *